United States Patent
Pandey et al.

(10) Patent No.: US 9,509,923 B2
(45) Date of Patent: Nov. 29, 2016

(54) CONTINUOUS INFRARED THERMOGRAPHY MONITORING AND LIFE MANAGEMENT SYSTEM FOR HEAT RECOVERY STEAM GENERATORS

(75) Inventors: Achalesh Kumar Pandey, Greenville, SC (US); Nirm Velumylum Nirmalan, Niskayuna, NY (US); Manoharan Venugopal, Bangalore (IN); David Lee Rogers, Marietta, GA (US); John Brandon Laflen, Niskayuna, NY (US); Lucy Summerville Giametta, Greenville, SC (US)

(73) Assignee: General Electric Company, Schenectady, NY (US)

(*) Notice: Subject to any disclaimer, the term of this patent is extended or adjusted under 35 U.S.C. 154(b) by 1328 days.

(21) Appl. No.: 13/346,755

(22) Filed: Jan. 10, 2012

(65) Prior Publication Data
US 2013/0176418 A1 Jul. 11, 2013

(51) Int. Cl.
*G01N 25/72* (2006.01)
*H04N 5/33* (2006.01)

(52) U.S. Cl.
CPC ............. *H04N 5/33* (2013.01); *G01N 25/72* (2013.01)

(58) Field of Classification Search
None
See application file for complete search history.

(56) References Cited

U.S. PATENT DOCUMENTS

| | | | |
|---|---|---|---|
| 3,504,524 A | 4/1970 | Maley | |
| 3,566,669 A | 3/1971 | Lawrence et al. | |
| 4,420,965 A | 12/1983 | Farkas et al. | |
| 4,885,633 A | 12/1989 | Buck | |
| 5,131,758 A | 7/1992 | Heyman et al. | |
| 6,422,743 B1 | 7/2002 | Nirmalan et al. | |
| 6,517,236 B2 | 2/2003 | Sun et al. | |
| 6,585,408 B2 | 7/2003 | El-Gabry et al. | |
| 6,732,582 B2 | 5/2004 | Bunker et al. | |
| 6,804,622 B2 * | 10/2004 | Bunker et al. | 702/134 |
| 7,040,805 B1 | 5/2006 | Ou et al. | |
| 8,209,133 B2 * | 6/2012 | Darehbidi et al. | 702/34 |
| 2005/0147150 A1 * | 7/2005 | Wickersham et al. | 374/120 |
| 2006/0086912 A1 * | 4/2006 | Weir et al. | 250/559.4 |
| 2006/0098872 A1 * | 5/2006 | Seo | G06K 9/209 382/181 |
| 2006/0191119 A1 * | 8/2006 | Coleman et al. | 29/402.01 |
| 2007/0154205 A1 * | 7/2007 | Kocanda et al. | 396/427 |
| 2009/0000382 A1 * | 1/2009 | Sathish et al. | 73/606 |
| 2009/0216574 A1 * | 8/2009 | Nuszen et al. | 705/7 |
| 2010/0073670 A1 * | 3/2010 | Furukawa et al. | 356/237.2 |
| 2011/0273702 A1 * | 11/2011 | Jones et al. | 356/51 |

* cited by examiner

*Primary Examiner* — James M Anderson, II
(74) *Attorney, Agent, or Firm* — Nixon & Vanderhye P.C.

(57) ABSTRACT

A method for continuously monitoring the working condition of a heat recovery steam generator ("HRSG") using infrared thermography, comprising the steps of identifying target locations inside the HRSG, positioning one or more infrared cameras to continuously monitor and record the temperature at each target location, generating continuous thermographic images corresponding to selected components and locations at each target locations, comparing the continuous thermographic images to corresponding, stored base line images and generating a set of comparative data reports in real time for each target location in order to predict the life span or potential failure of HRSG components.

16 Claims, 5 Drawing Sheets

CONTINUOUS INFRARED THERMOGRAPHY MONITORING AND LIFE MANAGEMENT SYSTEM FOR HEAT RECOVERY STEAM GENERATORS

The present invention relates to a method of using infrared ("IR") thermography in combination with a continuous review and analysis of accumulated thermography data for the purpose of monitoring and controlling the performance (and possible repair or replacement) of critical components in a heat recovery steam generator ("HRSG").

BACKGROUND OF THE INVENTION

For many years, a need has existed for a method to continuously monitor the performance of critical components of heat recovery steam generators in order to improve their long-term efficiency and reliability. The present invention provides a new approach to the capture, analysis and use of infrared thermography data for the purpose of improving the operation and reliability of key components of HRSGs, thereby reducing the possibility of a catastrophic failure of such systems and increasing their overall efficiency.

Many processes associated with gas turbine engines, particularly HRSGs, control excess thermal energy generated during their operation (such as the heat of combustion) by using the energy as a heat source for other systems. However, simply identifying and controlling a heat source or thermal pattern is not enough to identify and predict potential equipment failures. In order to be fully effective, the system needs to be capable of monitoring and detecting temperature changes to key pieces of equipment and then comparing any detected operational changes over time to corresponding control models. Once a base line thermal signature is obtained and understood for a particular piece of equipment, deviations from the normal temperature signature can provide valuable information regarding a developing or existing problem.

As detailed below, it has been found that infrared thermal imaging can be used effectively to identify a problem in HRSG components and help limit or control the root cause of any overheating or potential failure. In many cases, the heat generated by a defective component may only be indirectly visible to an IR camera as the heat conducts through the component and appears as a thermal gradient on the object surface. A need therefore exists for an IR thermography system that can accurately correlate IR data in real time to specific HRSG components or locations within the HRSG that can be continuously monitored or controlled.

The invention also contemplates the possibility of using other test equipment, such as vibration analysis tools, chemical analysis or even ultrasound, in combination with IR thermographs generated by an IR camera to help pinpoint the exact location and nature of an operational problem. Once a thermal anomaly is detected, the combination of IR and other tools can help isolate, control or rectify the root cause of the problem. The use of infrared thermography for condition monitoring as outlined below can also be adapted to components that are not directly associated with an HRSG, including various gas turbine mechanical systems (e.g., compressors, motors, turbines, rotors and pumps), or even electrical components (e.g., transformers, relays, switches, transmission lines, bus connections, fuses and even circuit breakers). Currently, HRSG plant operators monitor the operation and condition of equipment only routinely, normally waiting until a unit is shut down, e.g., in intervals of three to six months up to a year. During those occasions, periodic recorded temperature differences on the surface of selected components can be used to assess equipment operation based on target design criteria. However, as noted above, such occasional, infrequent monitoring is far less effective in predicting or preventing a catastrophic failure of HRSG components or other critical gas turbine equipment.

In the exemplary embodiments of the invention described below, the following definitions apply to certain key terms:

"Thermal sensitivity": The smallest change in IR radiation level that an IR camera is capable of recording (normally expressed in terms of a percentage of temperatures in degrees centigrade).

"Nominal temperature range": A temperature measurement from $-40°$ C. up to $2000°$ C. (the current operating range possible with most IR cameras).

"Environmental temperature": The range of temperature at which the IR camera may be safely operated without suffering from process conditions that could adversely affect performance.

"Thermal resolution": The smallest measurable difference in temperature between two related IR measurements over time.

"Spatial resolution": A measure of the fineness of detail in the IR image which is directly proportional to the number of pixels representing the image.

"IR accuracy": A measure of the difference between the true surface temperature and calculated temperature based on IR image data.

"Spot size ratio": The maximum distance the IR camera can be positioned from a target location, taking into account the size of the target and acceptable temperature measurement accuracy.

BRIEF DESCRIPTION OF THE INVENTION

By way of summary, the present invention comprises a method and system for continuously monitoring the working condition of a heat recovery steam generator using infrared thermography, wherein the steps include identifying specific target locations in the HRSG, positioning one or more infrared cameras inside the HRSG to continuously monitor and record the temperature at each target location, generating a set of continuous thermographic images corresponding to selected components (such as critical HRSG tubes and headers) at each target location, comparing the continuous thermographic images to corresponding stored base line IR images of the same target locations, and generating a continuous set of visual comparative data reports in real time for each of the target locations, with emphasis on predicting the life span and/or potential failure of specific HRSG components.

Exemplary embodiments of the invention also include a system for continuously monitoring the working condition of an HRSG that includes one or more IR cameras, a viewing port for mounting each IR camera inside the HRSG, integral IR camera windows, window cleaning means, a data acquisition system for accumulating IR data and image analysis software tools. In operation, the system is capable of continuously monitoring the temperature profile of selected HRSG tubes and headers on line while the plant is in running condition. An exemplary system includes one or more IR cameras positioned at predefined target locations inside the HRSG, adjustable 3-D mounting structures for the cameras, a plurality of thermocouples and transmitters capable of generating continuous infrared temperature data from each target location and source code for analyzing the output infrared data. In the end, the system continuously generates a set of thermographic images, compares those images to corresponding base line images and predicts the potential life span or possible failure of HRSG components.

It has been found that infrared thermal imaging according to the invention can provide a highly reliable condition-monitoring tool on a real time basis for HRSGs that significantly reduces maintenance costs and equipment failures over time. The monitoring and control steps described herein allow for on-site monitoring of temperatures and thermal patterns of key components while the equipment remains on line and running under normal process conditions. The operating temperature limits of different components being monitored serve as the critical control parameters and allow for a continuous comparison of actual and design criteria for the HRSG. The same basic infrared thermal imaging systems can be used on equipment that is related, directly or indirectly, to the HRSG, including smaller components, such as pumps, motors, bearings, pulleys, fans, drives, etc. Again, the accumulated IR thermography data permits potential and actual faults to be identified, isolated and resolved before a catastrophic failure occurs, and thus significantly reduces downtime resulting from equipment failures.

In order to continuously monitor key components in the HRSG, the invention uses a plurality of IR cameras to scan and record IR readings at key target locations on a continuous basis, each of which includes motorized mechanisms that allow the camera to be accurately positioned to monitor and survey critical pieces of HRSG equipment. The accumulated temperature data over time and IR observations are then analyzed to determine whether any process changes should be made or the component in question taken out of service for immediate repair. Such continuous, on-line temperature and condition monitoring represents a distinct improvement over previous non-contact monitoring techniques by providing an immediate, reliable and accurate temperature profile of almost any selected material surface.

Because every surface with a temperature above absolute zero emits at least some infrared radiation, thermography has been found to be a much more efficient surveillance technique for determining the general health of an HRSG over long periods of time. The infrared radiation emitted by a particular component is used to produce a thermal "map" of the surface being monitored at any fixed point in time. The resulting image map identifies temperature variations by displaying different colors (or shades of grey), and thus can be used for on-line monitoring of both electrical and mechanical equipment, e.g., by identifying unusual "hot spots" (or cold "dead" spots in electric circuits), as well as areas of equal temperature (isotherms) in base line images.

DETAILED DESCRIPTION OF THE INVENTION

Figure 1:
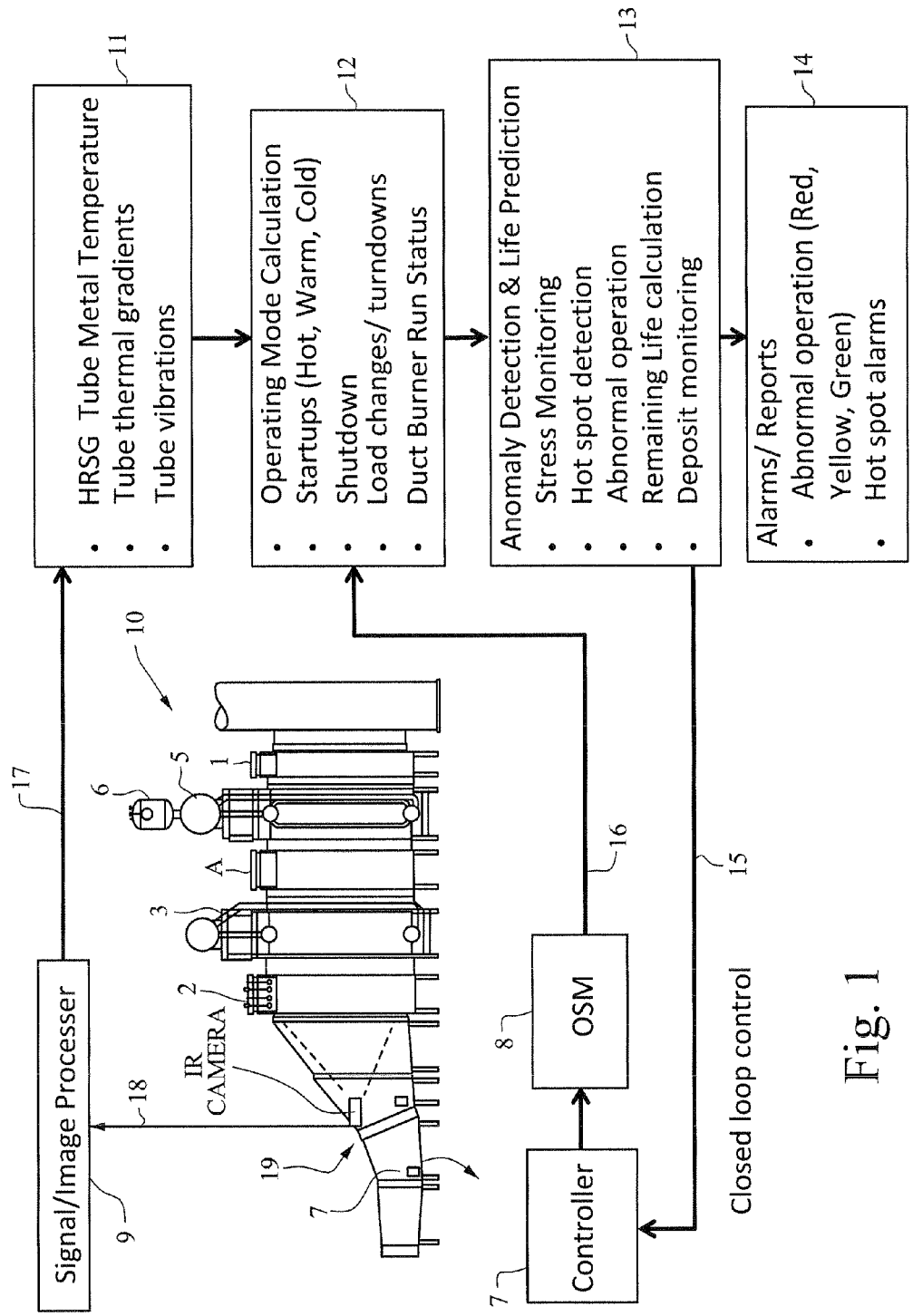
FIG. 1 is a schematic diagram of a continuous IR thermography monitoring system for a heat recovery steam generator according to the present invention.

As noted above, a typical infrared thermography monitoring and life management system for an HRSG in accordance with the invention consists of one or more thermal imaging devices (IR cameras), viewing ports for mounting the cameras inside the HRSG at pre-selected strategic locations, an IR window for each viewing port, window cleaning means, a data acquisition system, and image analysis software tools that monitor and analyze the detected temperature profiles of tubes, headers and other key components while the HRSG is still running. As one example, the invention has the ability to obtain thermal images in real time of HRSG boiler tubes over a large area and at strategic locations inside the HRSG. The measurements normally occur in a harsh environment, e.g., at operating temperatures approaching 650° C. or above, often in the presence of dust or other entrained particulates. Significantly, the IR image data accumulated over time can be used to effectively monitor and/or estimate HRSG tube vibrations occurring at different locations in the HRSG and thereby provide valuable data regarding the expected lifespan or potential failure of different target sets of HRSG tubes.

In particular, it has now been found that a reliable tube vibration analysis can be carried out on a continuous basis using the following basic steps: (1) installing one or more IR cameras (operated either manually or automatically) to monitor selected target HRSG tubes; (2) setting the IR camera(s) to continuously acquire relevant image data (e.g., using either a wireless or wired interface); (3) programming the IR camera(s) to first detect and then account for any vibration associated with the camera itself (for example, using a frame rate that exceeds, e.g., twice, the expected natural vibration frequency of the HRSG tubes being monitored and setting the camera pixel size to a level at or below the expected magnitude of tube vibration; (4) minimizing (if necessary) any local camera vibration by mechanically decoupling or isolating the IR camera from the HRSG tube frame; (5) determining the level of any residual local camera vibrations (e.g., using actuators or mechanical transducers which sense and count local camera vibrations); (6) acquiring continuous IR image data; and finally (7) analyzing the continuous IR image data over time by calculating a vibration estimate (and potential failure) of the target HRSG tubes.

In another aspect of the invention, the temperature of HRSG components (typically tubes and headers) currently are measured at only a few locations using previously installed thermocouples. Such data limits the accuracy of life prediction models and differs significantly from the present approach of real-time monitoring using IR thermography to measure and evaluate temperatures differences over large areas at multiple locations. The availability of temperature data at different locations over time, such as the identification of thermal gradients occurring during different cycles of operation of an HRSG, improves the life prediction accuracy of HRSG components and helps to locate abnormal thermal gradients and potential equipment failures during different cycles of operation.

The challenge of providing access to HRSG boiler tubes by IR thermal imaging devices is overcome by using a new viewing port window design capable of continuously transmitting infrared images in real time at frequencies near infrared ("NIR"), i.e., wavelengths of 0.9 to 1.7 microns and long wavelength IR ("LWIR") at wavelengths between 7.0 and 14.0 microns. The safety of operating and maintenance personnel also requires that the infrared radiation be transmitted at certain specified wavelengths. A mid-range IR camera can be used to perform the monitoring, but typically requires using germanium windows. For most NIR cameras, the viewport windows can comprise high quality silica, quartz or sapphire and provide clear views of the surface being monitored; the LWIR cameras transmit images at the longer wavelength using windows typically comprising ZnSe.

The design and construction of the viewing ports serve as an effective barrier to the hot gases and harsh interior HRSG environment, without compromising the pressure inside the HRSG. Nominally, the viewing ports include metal flanges welded directly to the HRSG interior with flexible mounting structures capable of handling any thermal expansion caused by HRSG gases. Since the pressure inside the HRSG remains close to atmospheric, the viewing windows normally do not need to withstand high internal pressures as long as they are capable of withstanding the high HRSG gas temperatures.

Exemplary IR windows useful in practicing the invention must also be protected from the accumulation of dust, which otherwise can reduce the quality of any thermal images (and potentially distort the analysis of thermography data over time). One solution to the potential dust problems is a secondary window that opens during the acquisition of the IR images. Another solution purges the windows with clean air (e.g., instrument air) to avoid contamination by hot gases. Yet another embodiment uses an electrically operated shutter in front of the IR window which likewise opens only during the acquisition of the images.

As briefly discussed above, preferred IR imaging cameras include those operating near infrared wavelengths (NIR) with a relatively wide viewing angle. Most NIR cameras have the advantage of using lenses and windows with a standard lens material. One minor disadvantage of the near infrared ("NIR") camera is that at temperatures approaching 650° C., the cameras tend to exhibit a lower signal to noise ratio. Other acceptable IR cameras (e.g., those using micro bolometer technology) operate at temperatures closer to 650° C. with a higher signal to noise ratio, however the lenses and windows must be made of special materials such as ZnSe or Germanium. For any type of camera, a high band pass filter (e.g., 1.5 microns) is also normally required to avoid any absorption/emission from the $CO_2$ and $H_2O$ in the hot HRSG gases.

In operation, the IR cameras are mounted at various locations in the HRSG to monitor the temperature profile of specific tubes, headers, tube joints and other key components exposed to the hot gases. The following locations are exemplary: the front portion of HRSG (in order to monitor tube temperature profile and vibrations); the back portion of the HRSG near the exhaust stack (to identify the cold-end temperature distribution and any tube deposits); the temperature distribution of the HRSG headers; and the tubes near the duct burner area. Exemplary camera speeds should have the ability to measure temperatures within a two degree centigrade accuracy and acquire data continuously with frame rates of about 30 frames per second.

Preferably, the IR cameras should be calibrated during planned HRSG downtimes in order to facilitate 3D-to-image surface mapping for any related data analysis software tools. The cameras can be calibrated for each anticipated camera viewpoint setting (e.g., pointing upwards toward the top of the HRSG or downward toward the bottom of the HRSG). Automatic tube detection algorithms then register the anticipated geometry of target components to the acquired IR images, thereby providing a basis for estimating camera length, range and precise location. A technique for automatically calibrating the IR cameras includes acquiring a dense sampling of images over the sweep range of the camera's expected viewpoints and then performing image-to-image map surface estimations using the camera geometry to adjust and calibrate each camera position to a corresponding viewpoint.

The images collected from the IR cameras are processed and various features (e.g., hot spot, cold spot, unusual temperature distributions, mean temperature values, etc.) are extracted and analyzed using software tools. The accumulated data values and other HRSG operating parameters are also fed to an anomaly detection and life prediction system which compares the accumulated information to base line design parameters (for example, metal creep, fatigue and tube wall thinning data). The same continuous stream of IR data can be used to facilitate closed loop control (e.g., ramp rate controls, etc.), or to generate alarms or make operation/maintenance recommendations. Currently, conventional HRSG monitoring systems rely almost entirely on steam temperature and metal temperature thermocouple readings (and only on an interim basis) for general life monitoring. The thermocouples are limited in utility because they only provide point measurements and the resulting algorithms do not account for thermal gradients occurring over time across the entire length of, for example, steam headers.

Normally, the IR camera systems useful in practicing the invention can be calibrated during planned HRSG downtimes. The calibration also facilitates the image-to-3D surface mapping performed by any data analysis software tools. In particular, the calibration accounts for specific parameters (such as focal length, pixel size, skew and image center), as well as data regarding lens distortion, camera position inside the HRSG and camera orientation relative to the target. Although camera performance and lens distortion often depend on view-orientation, normally each anticipated camera viewpoint setting will undergo at least some calibration.

One method for automatic calibration according to the invention uses the known 3D geometry of HRSG tubes within camera view and tube detection algorithms correlate the expected geometry to actual IR images using estimated focal lengths, ranges, locations, etc. Another method for automatic IR camera calibration relies on a dense sampling of images within the sweep range of the camera to create an image map of known and expected geometries within the camera's viewpoints. The sampling results in image-to-image mapping using the expected geometry within camera view.

Simultaneous with any camera calibration, a series of base line images is collected for reference in order to estimate motion blur (and possible tube vibration) when the HRSG is online. The set of base line images can be the same set as the densely sampled images used for calibration during online monitoring to estimate motion blur. Camera vibration can be accounted for as a form of spatial jitter that can be corrected using a spatial frequency filter to map the original scene (i.e., the base line image) onto any scene evidencing blur.

Turning to the figures, FIG. 1 is a schematic diagram of a continuous IR thermography monitoring system for a heat recovery steam generator according to the present invention. The HRSG, shown generally at 10, includes a plurality of IR cameras (preferably NIR) located at various strategic locations inside the HRSG and capable of providing continuous, real time monitoring of the condition of selected HRSG components. The HRSG depicted in the figure includes, as exemplary components, a low pressure economizer 1, super heater 2, high pressure evaporator 3, high pressure economizer 4, low pressure evaporator 5, integral deaerator 6 and duct burner 19.

FIG. 1 also identifies some of the candidate locations and properties that can be determined using thermography data generated by an IR camera as described above. By way of non-limiting example, the IR camera shown positioned near duct burner 19 provides a continuous IR thermography input signal 18 which is processed, along with other IR image data, by signal image processer 9. The processer in turn generates output temperature measurements 17 based on a comparison of accumulated IR data to base line calibration data including, for example, the HRSG tube metal temperature and relevant thermal gradients for the tubes as shown at temperature sensing step 11. In this example, some non-IR data could also be processed at the same time, such as the level of HRSG tube vibrations that fall outside a normal acceptable range.

FIG. 1 also illustrates an exemplary form of closed loop control by which the IR thermography data can be used to determine the operating conditions of the HRSG in real time, including process anomalies that fall outside a normal range or indicate malfunctions or potential equipment failures. Operating mode calculation step 12 includes, for example, the conditions at startup of the HRSG (hot, warm and cold), shutdown conditions, thermal load changes, "turndowns" of the system and duct burner run status all parameters indicating how the HRSG is operating over time. The operating mode calculations over time would nominally be carried out by a central computer (not shown) that receives and analyzes the relevant HRSG data over time and has the capability of issuing data reports and HRSG warnings or alarms in real time.

Data comparison step 13 as shown in FIG. 1 relates to the anomaly detection and life prediction described above using IR thermography and other data to determine, for example, stress monitoring of selected HRSG components, "hot spot" detection (temperatures above normal running conditions), abnormal operations, deposit monitoring and a calculation of the predicted life span of the target components being observed on a continuous basis. The comparative analysis conducted at step 13 is sent directly to HRSG controller 7 through closed loop control line 15 as shown. Controller 7 in turn functions to adjust, if necessary, the operation of the HRSG operations using on-site monitor ("OSM") 8 that provides feedback data used to make continuous operating mode calculations sent across OSM communications line 16. The OSM nominally includes separate computer means capable of communicating directly with a central computer handling the operating mode calculation step 12 of FIG. 1. As such, the OSM IR data can be continuously analyzed using image processing software to provide real time images and related date for the various HRSG components.

FIG. 1 also illustrates how an exemplary system can be used to generate an alarm signal and/or visual reports to the HRSG operators if, for example, the results of anomaly and detection step 13 indicate a potential failure mode for a target HRSG component. In this example, alarm step 14 would signal any abnormal operations which appear as red, yellow or green alarm codes, depending on the level of seriousness of the detected anomaly. "Hot spot alarms" can also be generated, alerting operating personnel to an urgent concern that requires immediate attention and/or shutdown.

Figure 2:
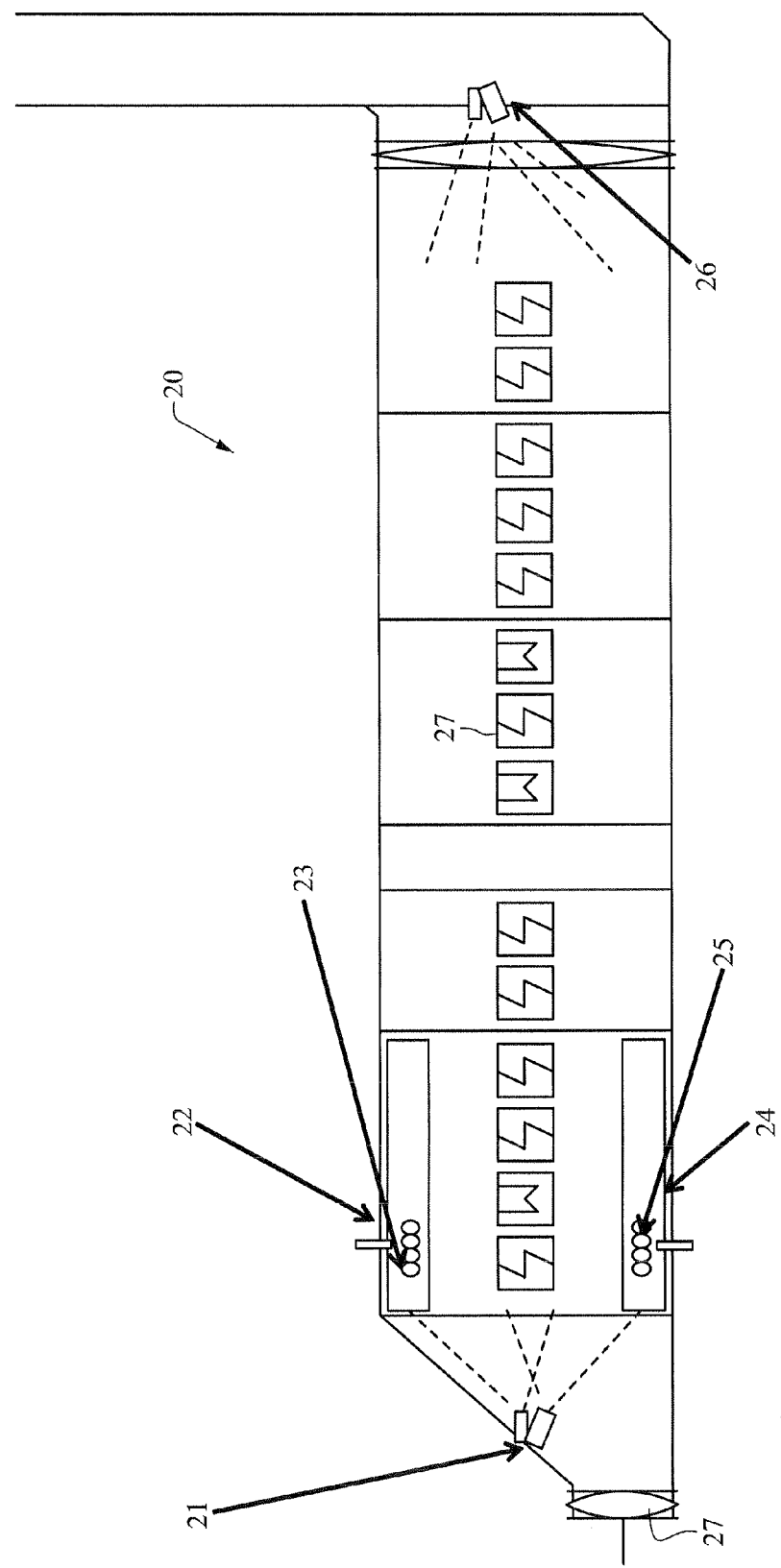
FIG. 2 is a cross-sectional view of the major components of an exemplary heat exchanger used in a heat recovery steam generator depicting various locations for implementing the continuous IR thermography monitoring system of the invention.

FIG. 2 is a cross-sectional view of the major components of a heat exchanger 20 (sometimes referred to as a "hot box") in an exemplary heat recovery steam generator depicting various locations for implementing the continuous IR thermography monitoring system of the invention. As FIG. 2 illustrates, front IR camera 21 can be positioned at the front end of the exchanger in order to monitor and determine a tube temperature profile. Significantly, front IR camera 21 (like the majority of cameras) has 3-D scanning capability sufficient to capture relative large areas of the tube bundles 27 and thus can be used to monitor a significant number of the headers and nozzles inside the hot box. In like manner, a separate IR camera 22 can be placed on top of the hot box as shown for purposes of monitoring the temperature of top headers 23. Back side IR camera 26 serves to monitor the tube temperature distribution as shown and detect unfavorable deposits and/or "cold spots" in that zone. IR camera 24 is positioned near the bottom hot box for purposes of monitoring the temperature of bottom headers 25.

Figure 3:
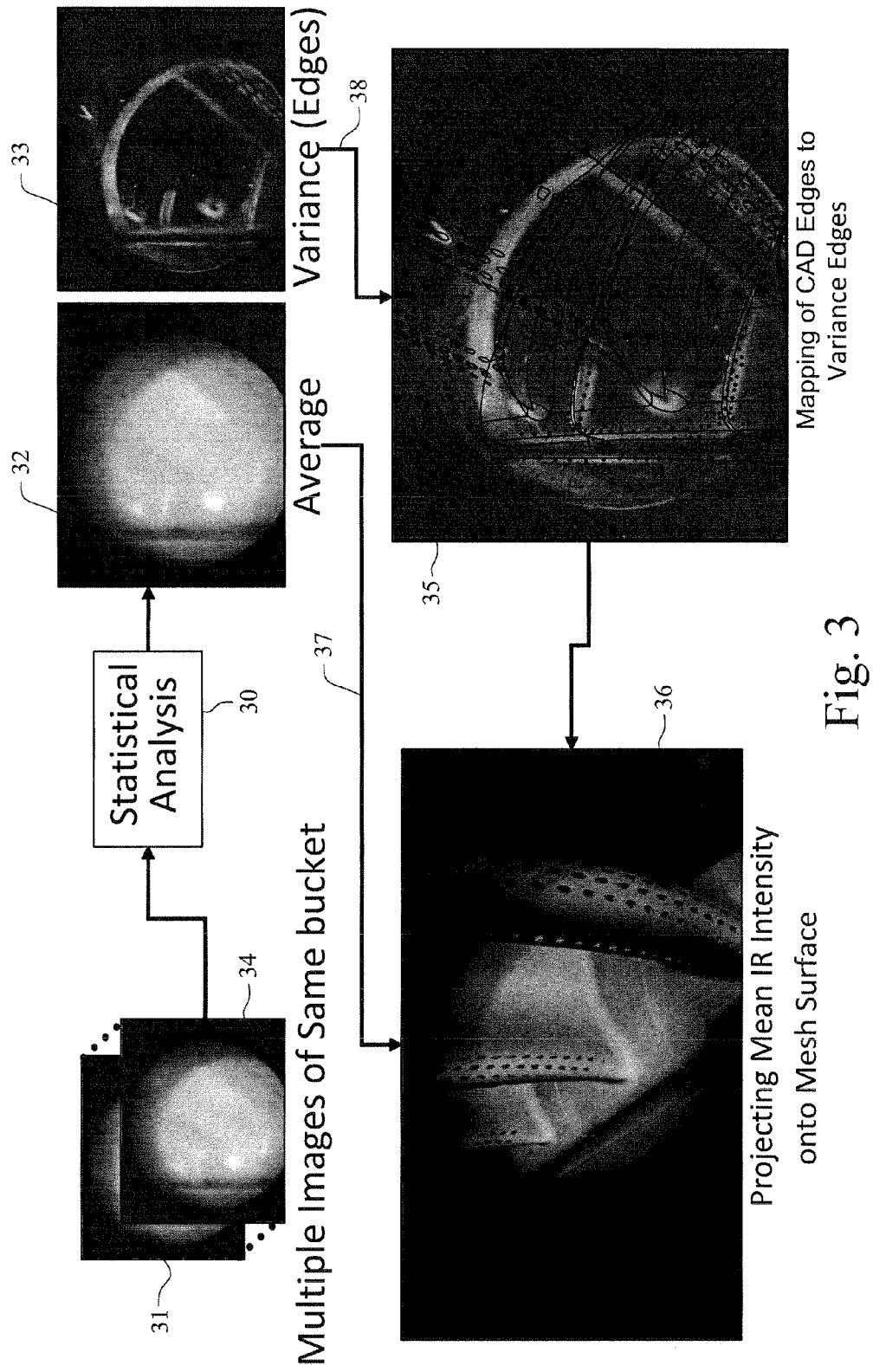
FIG. 3 is a series of infrared images depicting exemplary components of a gas turbine engine (rather than only in an HRSG) that can be monitored using the continuous IR thermography system according to the invention.

FIG. 3 is a series of infrared images depicting exemplary components that can be monitored using a continuous IR thermography system, in this example the condition and potential failure of gas turbine buckets. The same basic IR imaging approach and methodology could be applied to different target components of the HRSG. In the context of a gas turbine, multiple IR images 31 and 34 of a gas turbine bucket over time undergo a statistical analysis step 30 which leads to an average image data 32 which is compared to an average of base line data for the same bucket. The result is a calculated variance 33 (with the variance in FIG. 3 depicted along the bucket edges). The specific variance data 38 in turn is used to produce an IR image map 35 that transforms the data for the bucket edges into a computer aided design. The CAD data can be projected as shown in the solid CAD FIG. 36 to illustrate the mean IR intensity and variance edge data of interest.

Figure 4:
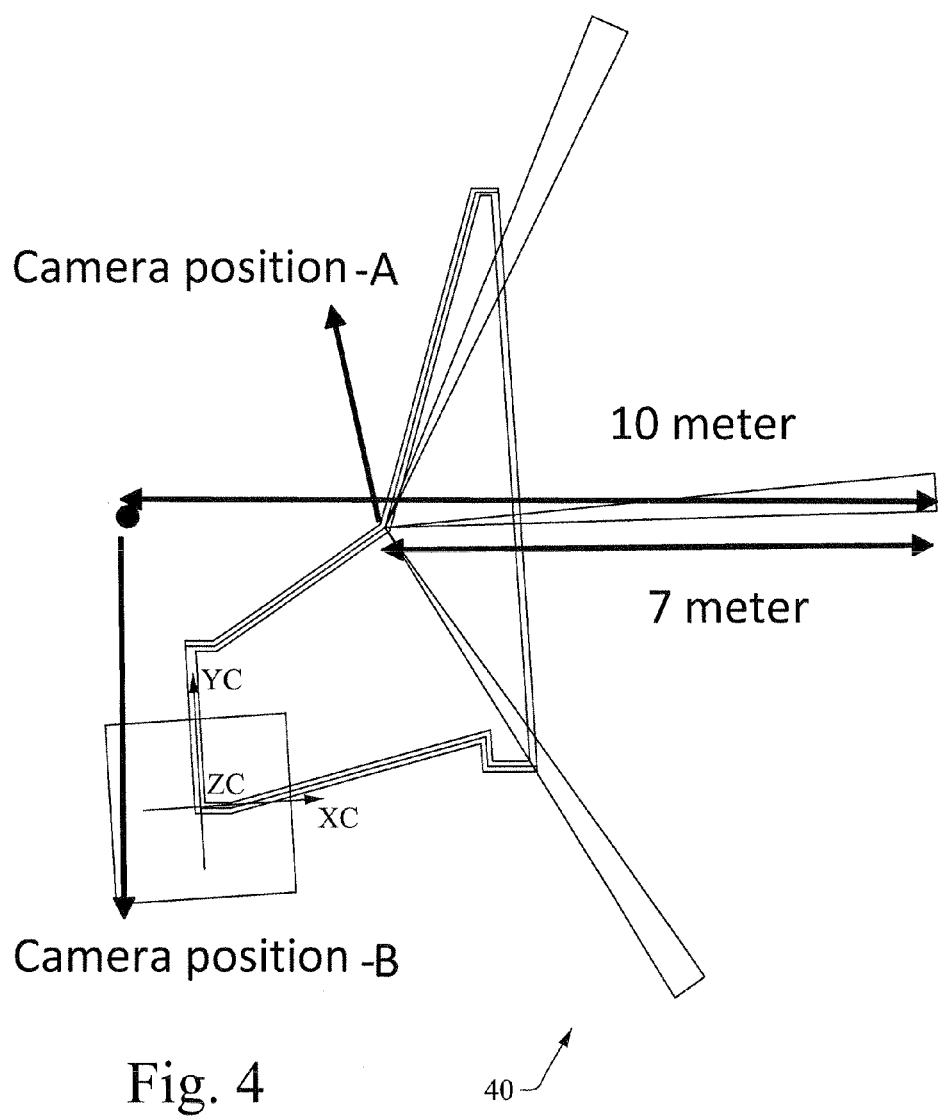
FIG. 4 is a schematic diagram identifying exemplary IR thermography camera positions and scanning profiles for a representative HRSG inlet.

FIG. 4 of the drawings is a schematic diagram depicting exemplary IR camera positions and scanning profiles 40 for a representative HRSG inlet line. FIG. 4 also depicts a representative view port located at the center of a gas inlet indicating that the camera can be positioned up or down in order to effectively scan a target HRSG component (see camera positions A and B), with potential movement of the camera in all three planes, in this example labeled "XC," "YC" and "ZC" for camera position B. As noted above, the view port must be capable of transmitting a "clean" infrared image, depending on the exact type of infrared camera being used. The view port must also serve as an effective barrier to the hot HRSG gases and maintain the pressure inside the HRSG, thereby serving as a shield to the separate inside atmosphere of the HRSG and yet be capable of accurately transmitting IR image data.

The view port for camera position A, on the other hand, allows for scanning in only one direction in this example. The port size for camera position A would be about 8 cm×6 cm; the port size for camera position B would be about 130 cm×90 cm and the FOV of the A camera would be approximately 25×18 degrees.

FIG. 4 also illustrates exemplary target planes and the positions of cameras A and B, i.e., the distance between the center of view port and the first row of tubes to be monitored, i.e., about 7 to 10 meters. In exemplary embodiments, the view ports can be attached to a metal flange welded to the HRSG that is designed to account for thermal expansion of the HRSG during, for example, startup or shutdown operations. Exemplary view port windows also must be protected in some manner from the accumulation of dust which otherwise could reduce the quality and accuracy of accumulated IR image data.

Preferably, each IR camera window should also be equipped with a cleaning mechanism, or perhaps secondary window that opens during the acquisition of images. Another design option uses clean shop air and/or pressurized instrument air to prevent the windows from being contaminated with dirt or dust from the hot HRSG gases. Yet another design option includes an electrically and/or mechanically operated shutter in front of each IR window that opens only during the taking of IR images.

Figure 5:
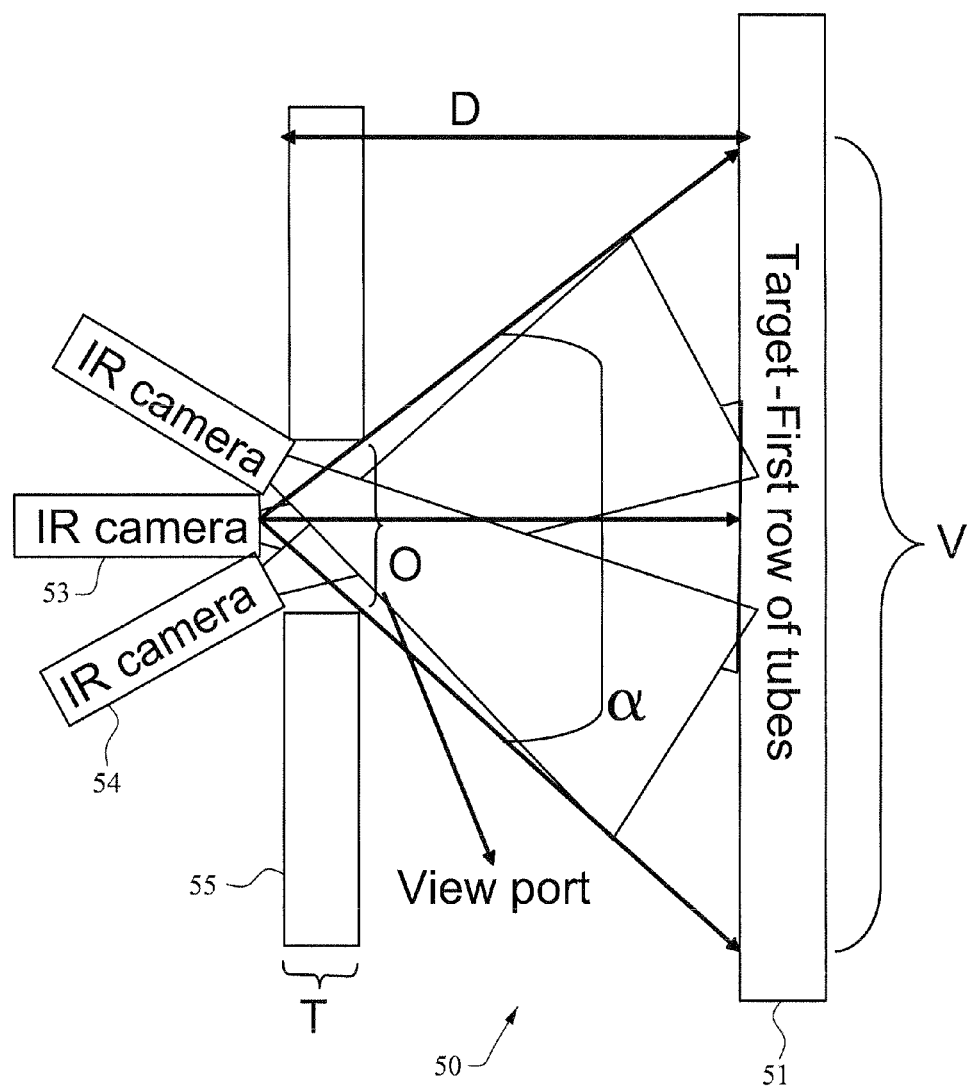
FIG. 5 is an optimization diagram depicting viewport target distances, viewing areas and viewing angles for an IR imaging system useful in practicing the invention.

Finally, FIG. 5 is an optimization diagram depicting exemplary viewport target distances, viewing areas and viewing angles for an IR imaging system useful in practicing the invention. In this example, three different IR cameras scanning positions are depicted with a separate view port "O" but different (potentially overlapping) viewing angles "α", with the target viewing area being the first row of tubes as shown. The following definitions apply to the labels in the figure. The letter "D" indicates the distance from the view port to the target; "V" is the vertical length of the viewing area; "T" identifies the tube wall thickness (in this example a gas inlet duct); "O" is the view port width; and "α" represents the angle subtended by the IR camera for view area V. View area vertical length V is established by first determining α for a given view port to target distance D and then calculating the width of the view port for each different α and wall thickness.

Generally, the relevant IR thermography measurements described above can be accomplished in four basic steps: (1) transforming the received infrared radiation data into an electrical signal that is then output for review, data accumulation and analysis; (2) compensating for background radiation due to the surface temperature of the object being imaged; (3) performing a linearization of the accumulated data; and (4) outputting the most relevant IR information on a continuous basis. Preferably, all four steps will be facilitated using software tools to ensure a continuous review and real time analysis of the accumulated data.

During start-up operations, the IR data can be compared and correlated to actual temperature data taken over time at specific target locations within the HRSG. Various types of conventional thermal detectors can be used to obtain the base line data, including thermocouples and possibly thermopile detectors, which include a plurality of thermocouples connected serially or in parallel, depending on the data being accumulated. Such detectors typically rely on an electrical potential produced as a measure of detected temperature difference. For example, the heat flow from an object to a thermocouple creates a perceptible temperature difference between the hot and cold junctions which results in an increase in the output electric signal. Most thermocouples include two different thermoelectric materials placed on a thin diaphragm having low thermal conductance and capacitance which create a temperature difference between hot and cold regions. In the various embodiments described above, a thermopile which is serially interconnected to an array of thermocouples to provide relevant input data can also be used.

As previously noted, the continuous IR monitoring technique of the invention can also be used on various HRSG components indirectly related to the HRSG. For example, steam turbine extraction points can be monitored and identified using the same basic IR techniques. Steam is tapped from various locations in order to power equipment and for other processes in the cycle. The fluid normally remains at high temperature (200 to 800° F.) and moderate pressure (7 to 700 psig) and thus can cause serious damage to equipment, piping and buildings. A problem detected by infrared imaging of the crossover piping on the turbine and condenser walls can show temperatures and patterns different from normal.

As another example, continuous IR thermography images of electric motors or generators can be a valuable key in a predictive maintenance program. All motors have a normal thermal pattern, as well as given maximum operating temperature. Most motors are designed to operate in ambient temperatures that do not exceed 40° C. Conditions such as inadequate air flow, partial discharge, unbalanced voltage, bearing failure, insulation failure and degradation in the rotor or stator can be identified with an infrared thermal imaging monitoring program of this kind. Abnormal thermal patterns can also identify misalignment in couplings when other rotating equipment is used in conjunction with the motors.

Existing and potential pump bearing problems can also be identified by making a comparison of surface temperatures using the above IR technique, i.e., by comparing one bearing to another working under similar conditions. Bearing overheating conditions can then be documented as hot spots within the infrared camera. For example, infrared thermal imaging can confirm that a lower thrust bearing is warmer than other bearings in the pump, perhaps indicating an imminent malfunction.

A similar continuous infrared thermal imaging can also be used to detect condenser air in-leakage problems that decrease the condenser's efficiency and create backpressure on a steam turbine, lowering its efficiency. IR imaging cameras can also continuously monitor and detect delamination on condenser rupture disk surfaces. Thermal anomalies of steam condensers are yet another example of the on-line IR monitoring using thermography according to the invention, by identifying cooling in areas of air in-leakage.

The continuous monitoring of electrical distribution systems using IR thermography also helps to identify actual and potential failures of electrical components, such as circuit breakers, transformers, bus bars etc. Most faults are encountered in the form of hot spots at contact terminals, which may be due to loose contact, corrosive nuts & bolts, broken conductor strands etc., and reflect a higher surface temperature. On-line thermal scanning of the contact terminals can identify the hot-spots and severity of the fault and improve reliability.

While the invention has been described in connection with what is presently considered to be the most practical and preferred embodiment, it is to be understood that the invention is not to be limited to the disclosed embodiment, but on the contrary, is intended to cover various modifications and equivalent arrangements included within the spirit and scope of the appended claims.

What is claimed is:

1. A method for continuously monitoring the working condition of a heat recovery steam generator ("HRSG") using infrared thermography, the method comprising:

identifying one or more target locations inside said heat recovery steam generator;

positioning one or more infrared cameras inside said heat recovery steam generator for continuously viewing said target locations;

capturing at least one image of the one or more target locations using the one or more infrared cameras, while the HRSG is in a downtime condition and not heated by a hot gas stream flowing through the HRSG;

calibrating the one or more infrared cameras, wherein the calibration includes estimating an optimum focal length and range for each of said one or more infrared cameras using tube detection algorithms which detect one or more tubes in the captured images of the target locations;

designating at least one image captured while the HRSG is in downtime as a corresponding base line image or images of the one or more target locations;

after calibrating the one or more infrared cameras and while the HRSG is operating to recover heat from a gas stream, capturing at least one image of the one or more target locations using the one or more infrared cameras;

generating a set of continuous thermographic images for each of said target locations using images captured by the one or more infrared cameras, while the HRSG is operating to recover heat from the hot gas stream passing through the HRSG;

comparing said continuous thermographic images to the corresponding base line image or images of the one or more target locations; and generating a set of comparative data reports and comparative images based on real time data accumulated for each of said one or more target locations and based on the comparisons of the thermographic images to the corresponding base line images.

2. A method according to claim 1, wherein said step of identifying said target locations includes identifying specific tubes or headers inside said heat recovery steam generator.

3. A method according to claim 1, wherein at least one of said infrared cameras is positioned at the front of said heat recovery steam generator to continuously monitor and record tube temperature profiles.

4. A method according to claim 1, wherein said source code predicts the anticipated life before failure of selected components of said heat recovery steam generator.

5. A method according to claim 1, further comprising the step of generating image-to-3D mapping of the surfaces of components within said target locations based on accumulated infrared data.

6. A method according to claim 1, further comprising the step of installing one or more high band pass filters to prevent the absorption of carbon dioxide and water by said infrared cameras.

7. A method according to claim 1, wherein said infrared cameras monitor the cold end temperature of selected tubes and headers at the back of said heat recovery steam generator.

8. A method according to claim 1, wherein said step of generating a set of continuous thermographic images uses thermocouples installed at each of said target locations.

9. A method according to claim 1, wherein said step of generating a continuous set of thermographic images are used to monitor and analyze tube vibrations occurring at different locations within the HRSG.

10. A method according to claim 9, wherein said step of monitoring and analyzing tube vibrations further comprises predicting the expected lifespan and potential failure of selected HRSG tubes.

11. A system for continuously monitoring the working condition of a heat recovery steam generator ("HRSG") using infrared thermography, comprising:

one or more infrared cameras positioned at target locations inside said heat recovery steam generator;

adjustable mounting structures for each of said infrared cameras, said mounting structures being secured inside said heat recovery steam generator near said target locations;

one or more infrared data transmitters for each of said infrared cameras generating continuous infrared data for each of said target locations;

one or more infrared data receivers generating a continuous set of thermographic images based on said infrared data; and a controller running source code to compare said continuous set of thermographic images to corresponding base line images of the same target locations, wherein the base line images are captured while the HRSG is down and unheated by a hot gas stream, wherein the controller generates an image-to-3D mapping of the surface of components located within said target locations and includes tube detection algorithms for estimating camera focal length and range.

12. A system according to claim 11, wherein said continuous set of thermographic images generated by said data receivers are used to monitor and analyze tube vibrations occurring at different locations within the HRSG.

13. A system according to claim 11, wherein said infrared cameras continuously transmit data at wavelengths near infrared between 0.9 and 1.7 microns.

14. A system according to claim 11, wherein said infrared cameras continuously transmit data at long infrared wavelengths between 7.0 and 14 microns.

15. A method for continuously analyzing infrared thermography data corresponding to target locations inside a heat recovery steam generator (HRSG), comprising the steps of:

positioning one or more infrared cameras inside said heat recovery steam generator for continuously viewing said target locations;

calibrating the one or more infrared cameras by estimating an optimum focal length and range for said infrared cameras using tube detection algorithms to detect tubes in images captured by the one or more infrared cameras of the target locations, while no hot gas stream passes the target locations of the HRSG;

generating base line infrared data on the target locations in the HRSG using images captured by the one or more infrared cameras of the target locations while no hot gas stream passes the target locations of the HRSG;

transforming received infrared data captured by the one or more infrared cameras, while a hot gas stream passes the target locations of the HRSG, into an electrical signal that can be output for data accumulation and analysis;

compensating for background radiation due to the surface temperature at each of said target locations;

performing a linearization of accumulated infrared data;

generating comparative thermographic images based on said accumulated infrared data and the base line infrared data for each of said target locations; and generating data reports of said comparative thermographic images.

16. A method for analyzing tube vibrations occurring in a heat recovery steam generator (HRSG), comprising the steps of:

installing one or more infrared (IR) cameras, said IR cameras being positioned to selectively image one or more target HRSG tubes;

calibrating the one or more IR cameras by estimating an optimum focal length and range for said IR cameras using tube detection algorithms to detect the one or more target HRSG tubes in images generated by the one or more IR cameras, while no hot gas stream flow through the target locations of the HRSG;

generating base line infrared data on the target locations in the HRSG using images captured by the one or more infrared cameras of the target locations while no hot gas stream passes the target locations of the HRSG;

continuously acquiring thermographic image data of said target HRSG tubes while hot gases flow through the HRSG;

determining the rate of vibrations of said one or more IR cameras based on comparisons of the base line infrared data and the continuously acquired thermographic image data;

acquiring continuous IR image data of said target HRSG tubes; and analyzing said continuous IR image data and said rate of IR camera vibrations to determine the vibration rate or potential failure of said target HRSG tubes.

\* \* \* \* \*